US010138576B2

(12) United States Patent
Scholz et al.

(10) Patent No.: US 10,138,576 B2
(45) Date of Patent: Nov. 27, 2018

(54) BIOCOMPATIBLE HYDROPHILIC COMPOSITIONS

(71) Applicant: 3M INNOVATIVE PROPERTIES COMPANY, St. Paul, MN (US)

(72) Inventors: Matthew T. Scholz, Woodbury, MN (US); Francis E. Porbeni, Woodbury, MN (US); Jay M. Jennen, Forest Lake, MN (US); Korey W. Karls, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 232 days.

(21) Appl. No.: 14/487,134

(22) Filed: Sep. 16, 2014

(65) Prior Publication Data

US 2015/0004866 A1    Jan. 1, 2015

Related U.S. Application Data

(63) Continuation of application No. 12/997,398, filed as application No. PCT/US2009/047057 on Jun. 11, 2009, now Pat. No. 8,858,986.

(60) Provisional application No. 61/061,088, filed on Jun. 12, 2008.

(51) Int. Cl.
*D01F 6/62* (2006.01)
*A61L 15/26* (2006.01)
*A61L 15/46* (2006.01)
*A61L 15/48* (2006.01)
*C08L 67/02* (2006.01)
*C08L 67/04* (2006.01)
*D01F 1/10* (2006.01)
*A01N 25/30* (2006.01)
*A41D 13/12* (2006.01)
*B29C 39/00* (2006.01)
*B29C 44/00* (2006.01)
*A61L 31/04* (2006.01)
*D04H 1/435* (2012.01)
*D04H 1/4382* (2012.01)
*A61B 46/00* (2016.01)
*C08K 5/053* (2006.01)
*C08K 5/098* (2006.01)
*C08K 5/103* (2006.01)
*C08K 5/41* (2006.01)
*C08K 5/42* (2006.01)
*C08K 5/51* (2006.01)
*C08L 71/02* (2006.01)

(52) U.S. Cl.
CPC .............. *D01F 6/62* (2013.01); *A01N 25/30* (2013.01); *A41D 13/1209* (2013.01); *A61B 46/40* (2016.02); *A61L 15/26* (2013.01); *A61L 15/46* (2013.01); *A61L 15/48* (2013.01); *A61L 31/048* (2013.01); *B29C 39/003* (2013.01); *B29C 44/00* (2013.01); *C08L 67/02* (2013.01); *C08L 67/04* (2013.01); *D01F 1/10* (2013.01); *D01F 6/625* (2013.01); *D04H 1/435* (2013.01); *D04H 1/4382* (2013.01); *A61L 2300/404* (2013.01); *A61L 2300/80* (2013.01); *A61L 2300/802* (2013.01); *C08K 5/053* (2013.01); *C08K 5/098* (2013.01); *C08K 5/103* (2013.01); *C08K 5/41* (2013.01); *C08K 5/42* (2013.01); *C08K 5/51* (2013.01); *C08L 71/02* (2013.01); *Y10T 442/30* (2015.04); *Y10T 442/60* (2015.04); *Y10T 442/674* (2015.04); *Y10T 442/68* (2015.04); *Y10T 442/681* (2015.04); *Y10T 442/689* (2015.04)

(58) Field of Classification Search
CPC ...................................................... D01F 6/62
See application file for complete search history.

(56) References Cited

U.S. PATENT DOCUMENTS

| | | |
|---|---|---|
| 1,975,504 A | 10/1934 | Formhals |
| RE24,906 E | 12/1960 | Ulrich |
| 3,121,021 A | 2/1964 | Copeland |
| 3,389,827 A | 6/1968 | Abere |
| 3,485,706 A | 12/1969 | Evans |
| 3,565,985 A | 2/1971 | Schrenk |
| 3,575,782 A | 4/1971 | Hansen |
| 3,637,900 A | 1/1972 | Kimura et al. |
| 3,816,229 A | 6/1974 | Bierbrauber |
| 3,825,379 A | 7/1974 | Lohkamp |
| 3,825,380 A | 7/1974 | Harding |
| 3,849,241 A | 11/1974 | Butin |
| 3,874,886 A | 4/1975 | Levecque |
| 3,896,251 A | 7/1975 | Landucci |
| 4,024,178 A | 5/1977 | Landucci |

(Continued)

FOREIGN PATENT DOCUMENTS

| | | |
|---|---|---|
| CN | 1749316 | 3/2006 |
| DE | 10 2007 030 159 | 1/2009 |

(Continued)

OTHER PUBLICATIONS

Lee, Combined effect of oleic acid and polyethylene glycol 200 on buccal permeation of [D-Ala2, D-Leu5]encephalin from a cubic phase of glyceryl monooleate, International Journal of Pharmaceutics, 2000, 204, 137-144.*

(Continued)

*Primary Examiner* — Paul W Dickinson
(74) *Attorney, Agent, or Firm* — 3M Innovative Properties Company; Carlos M. Téllez

(57) ABSTRACT

Durable hydrophilic compositions comprising aliphatic polyester, an anionic surfactant, and in some embodiments, a carrier.

25 Claims, No Drawings

(56) References Cited

U.S. PATENT DOCUMENTS

| | | |
|---|---|---|
| 4,054,592 A | 10/1977 | Dear |
| 4,103,058 A | 7/1978 | Humlicek |
| 4,112,213 A | 9/1978 | Waldman |
| 4,118,531 A | 10/1978 | Hauser |
| 4,134,951 A | 1/1979 | Dow et al. |
| 4,310,509 A | 1/1982 | Berglund |
| 4,323,557 A | 4/1982 | Rosso |
| 4,363,646 A | 12/1982 | Torobin |
| 4,401,780 A | 8/1983 | Steel |
| 4,448,983 A | 5/1984 | Young |
| 4,477,498 A | 10/1984 | Deiner |
| 4,536,361 A | 8/1985 | Torobin |
| 4,540,479 A | 9/1985 | Sakurai |
| 4,606,737 A | 8/1986 | Stern |
| 4,668,406 A | 5/1987 | Chang |
| 4,705,820 A | 11/1987 | Wang et al. |
| 4,737,410 A | 4/1988 | Kantner |
| 4,744,365 A | 5/1988 | Kaplan |
| 4,863,779 A | 9/1989 | Daponte |
| 5,016,331 A | 5/1991 | Dilo |
| 5,027,803 A | 7/1991 | Scholz |
| 5,045,387 A | 9/1991 | Schmalz |
| 5,227,107 A | 7/1993 | Dickenson |
| 5,268,733 A | 12/1993 | Wright |
| 5,364,694 A | 11/1994 | Okada |
| 5,382,400 A | 1/1995 | Pike |
| 5,427,842 A | 6/1995 | Bland |
| 5,475,063 A | 12/1995 | Kaplan |
| 5,496,507 A | 3/1996 | Angadjivand |
| 5,496,603 A | 3/1996 | Riedel |
| 5,502,160 A | 3/1996 | Modrak |
| 5,525,706 A | 6/1996 | Gruber |
| 5,585,056 A | 12/1996 | Liu |
| 5,589,122 A | 12/1996 | Leonard |
| 5,599,602 A | 2/1997 | Leonard |
| 5,631,073 A | 5/1997 | Riedel |
| 5,639,466 A | 6/1997 | Ford et al. |
| 5,660,922 A | 8/1997 | Herridge |
| 5,679,190 A | 10/1997 | Riedel |
| 5,698,322 A | 12/1997 | Tsai |
| 5,731,062 A | 3/1998 | Kim |
| 5,741,563 A | 4/1998 | Mehta |
| 5,753,736 A | 5/1998 | Bhat |
| 5,833,787 A | 11/1998 | Ehret |
| 5,883,199 A | 3/1999 | McCarthy |
| 5,910,368 A | 6/1999 | Ehret |
| 5,951,993 A | 9/1999 | Scholz et al. |
| 5,952,088 A | 9/1999 | Tsai |
| 5,952,433 A | 9/1999 | Wang |
| 5,997,568 A | 12/1999 | Liu |
| 6,005,019 A | 12/1999 | Liu |
| 6,045,908 A | 4/2000 | Nakajima et al. |
| 6,075,118 A | 6/2000 | Wang |
| 6,093,792 A | 7/2000 | Gross |
| 6,111,060 A | 8/2000 | Gruber |
| 6,114,017 A | 9/2000 | Fabbricante |
| 6,117,928 A | 9/2000 | Hiltunen |
| 6,121,170 A | 9/2000 | Tsai |
| 6,127,485 A | 10/2000 | Klun |
| 6,143,863 A | 11/2000 | Gruber |
| 6,183,670 B1 | 2/2001 | Torobin |
| 6,196,752 B1 | 3/2001 | Komiyama |
| 6,197,237 B1 | 3/2001 | Tsai |
| 6,232,280 B1 | 5/2001 | Shah |
| 6,261,677 B1 | 7/2001 | Tsai |
| 6,262,180 B1 | 7/2001 | Klun |
| 6,300,258 B1 | 10/2001 | Stano et al. |
| 6,306,782 B1 | 10/2001 | Tsai |
| 6,309,988 B1 | 10/2001 | Tsai et al. |
| 6,315,806 B1 | 11/2001 | Torobin |
| 6,342,566 B2 | 1/2002 | Burkhardt |
| 6,382,526 B1 | 5/2002 | Reneker |
| 6,384,142 B1 | 5/2002 | Burkhardt |
| 6,482,341 B1 | 11/2002 | Jongboom |
| 6,506,873 B1 | 1/2003 | Ryan |
| 6,515,054 B1 | 2/2003 | Matsushita |
| 6,548,431 B1 | 4/2003 | Bansal et al. |
| 6,645,618 B2 | 11/2003 | Hobbs |
| 6,743,273 B2 | 6/2004 | Chung |
| 6,787,493 B1 | 9/2004 | Nagaoka |
| 6,800,226 B1 | 10/2004 | Gerking |
| 6,861,025 B1 | 3/2005 | Erickson |
| 6,905,987 B2 | 6/2005 | Noda et al. |
| 6,916,480 B2 | 7/2005 | Anderson |
| 6,916,752 B2 | 7/2005 | Berrigan |
| 6,949,288 B2 | 9/2005 | Hodge et al. |
| 6,960,642 B2 | 11/2005 | Jariwala |
| 7,195,658 B2 | 3/2007 | Swei et al. |
| 7,199,197 B2 | 4/2007 | Caldwell |
| 7,241,838 B2 | 7/2007 | Shelby |
| 7,456,306 B2 | 11/2008 | Wolfgang et al. |
| 7,604,859 B2 | 10/2009 | Liu |
| 7,623,339 B2 | 11/2009 | Takahashi |
| 7,767,120 B2 | 8/2010 | Yahata et al. |
| 7,837,814 B2 | 11/2010 | Minami et al. |
| 8,287,509 B2 | 10/2012 | Joubert et al. |
| 8,721,943 B2 | 5/2014 | Moore et al. |
| 8,858,986 B2 | 10/2014 | Scholz et al. |
| 8,932,704 B2 | 1/2015 | Porbeni et al. |
| 2002/0188041 A1 | 12/2002 | Bond et al. |
| 2004/0009210 A1 | 1/2004 | Koenig et al. |
| 2004/0024141 A1 | 2/2004 | Hasebe |
| 2004/0045145 A1 | 3/2004 | Wang |
| 2004/0096656 A1 | 5/2004 | Bond |
| 2004/0126578 A1 | 7/2004 | Tsai et al. |
| 2004/0241216 A1 | 12/2004 | Klun |
| 2004/0265516 A1 | 12/2004 | Schulz |
| 2005/0026802 A1 | 2/2005 | Kilkenny et al. |
| 2005/0048152 A1 | 3/2005 | Gerking |
| 2005/0136781 A1 | 6/2005 | Lassig et al. |
| 2005/0233142 A1 | 10/2005 | Takahashi et al. |
| 2006/0058470 A1 | 3/2006 | Rizk |
| 2006/0058868 A1 | 3/2006 | Gale et al. |
| 2006/0084340 A1 | 4/2006 | Bond |
| 2006/0273495 A1 | 12/2006 | Topolkaraev |
| 2006/0276092 A1 | 12/2006 | Topolkaraev |
| 2007/0270071 A1 | 11/2007 | Greer |
| 2008/0038976 A1 | 2/2008 | Berrigan |
| 2008/0086199 A1 | 4/2008 | Dave |
| 2008/0142023 A1 | 6/2008 | Schmid |
| 2008/0160861 A1 | 7/2008 | Berrigan |
| 2008/0200890 A1 | 8/2008 | Wood |
| 2008/0213595 A1 | 9/2008 | Levitt |
| 2011/0065573 A1 | 3/2011 | McEneany et al. |
| 2011/0151737 A1 | 6/2011 | Moore et al. |
| 2011/0189463 A1 | 8/2011 | Moore et al. |
| 2012/0040185 A1 | 2/2012 | Topolkaraev et al. |
| 2012/0077886 A1 | 3/2012 | Scholz et al. |
| 2012/0088424 A1 | 4/2012 | Moore et al. |
| 2013/0210308 A1 | 8/2013 | McEneany et al. |
| 2013/0210949 A1 | 8/2013 | Scholl et al. |
| 2013/0288556 A1 | 10/2013 | Moore et al. |
| 2014/0210141 A1 | 7/2014 | Moore et al. |
| 2015/0004866 A1 | 1/2015 | Scholz et al. |

FOREIGN PATENT DOCUMENTS

| | | |
|---|---|---|
| EP | 0 527 489 | 2/1993 |
| EP | 569154 | 11/1993 |
| EP | 669358 | 8/1995 |
| EP | 1200661 | 7/2004 |
| EP | 1097967 | 12/2004 |
| EP | 1 604 813 | 12/2005 |
| EP | 1721927 | 11/2006 |
| EP | 1862507 | 12/2007 |
| JP | S56-159339 | 12/1981 |
| JP | H5-51852 | 3/1993 |
| JP | 61-66943 | 6/1994 |
| JP | H6-166943 | 6/1994 |
| JP | H06-184817 | 7/1994 |
| JP | H07-048768 | 2/1995 |
| JP | 10-017757 | 1/1998 |
| JP | H10-036652 | 2/1998 |
| JP | H11-131354 | 5/1999 |

(56) References Cited

FOREIGN PATENT DOCUMENTS

| | | |
|---|---|---|
| JP | 2000-96416 | 4/2000 |
| JP | 2000-136479 | 5/2000 |
| JP | 2003-245510 | 9/2003 |
| JP | 2003-286659 | 10/2003 |
| JP | 2004-532360 | 10/2004 |
| JP | H06-285112 | 10/2004 |
| JP | 2006-028726 | 2/2006 |
| JP | 2006-183180 | 7/2006 |
| JP | 2007-197857 | 8/2007 |
| JP | 2008-535955 | 9/2008 |
| JP | 4-319169 | 8/2009 |
| JP | 2009-221618 | 10/2009 |
| KR | 10-1999-0076593 | 7/1997 |
| KR | 10-0640138 | 10/2006 |
| WO | WO 1984-004311 | 11/1984 |
| WO | WO 1994-007941 | 4/1994 |
| WO | WO 1994-007949 | 4/1994 |
| WO | WO 1996-022330 | 7/1996 |
| WO | WO 1997-019991 | 6/1997 |
| WO | WO 1998-024951 | 6/1998 |
| WO | WO 1998-050611 | 11/1998 |
| WO | WO 1999-006456 | 2/1999 |
| WO | WO 1999-050345 | 10/1999 |
| WO | WO 2000-012606 | 3/2000 |
| WO | WO 2001-009425 | 2/2001 |
| WO | WO 2001/46507 | 6/2001 |
| WO | WO 2001/48303 | 7/2001 |
| WO | WO 2003-040201 | 5/2003 |
| WO | WO 2004/045663 | 6/2004 |
| WO | WO 2006/129731 | 12/2006 |
| WO | WO 2006-130211 | 12/2006 |
| WO | WO 2008-038350 | 4/2008 |
| WO | WO 2008/073099 | 6/2008 |
| WO | WO 2009/078849 | 6/2009 |
| WO | WO 2009-152349 | 12/2009 |
| WO | WO 2010-021911 | 2/2010 |
| WO | WO 2010-117612 | 10/2010 |
| WO | WO 2011-075619 | 6/2011 |
| WO | WO 2011-084670 | 7/2011 |
| WO | WO 2014/059239 A1 | 4/2014 |

OTHER PUBLICATIONS

Product Data Sheet on Calcium Stearate from Pratham Stearchem Pvt, Ltd; 2010; 1 pg.
Bansal, "On-Line Determination of Density and Crystallinity During Melt Spinning", Polymer Engineering and Science, Nov. 1996, vol. 36, No. 2, pp. 2785-2798.
Davies, "The Separation of Airborne Dust and Particles", Inst. of Mech. Engineers Proceedings, vol. 1B, 1952, pp. 185-198.
Fenner, "Principles of Polymer Processing", 1979, pp. 77-84.
Fink, "Ziegler Catalysts—Recent Scientific Innovations and Technological Improvements", Springer-Verlag, Berlin Heidelberg, 1995, 5 pages.
Gedde, "Polymer Physics", 1st Ed. Chapman & Hall, London, 1996, pp. 298.
Gokel, "Dean's Handbook of Organic Chemistry—Section 1 Organic Compounds", Second Edition, Kenneth P. McCombs, McGraw-Hill, 2004, pp. 1.18-1.22.
Kricheldorf, Chemosphere—Synthesis and Application of Polylactides, vol. 43, 2001, pp. 49-54.
Leenslag, "Resorbable Materials of Poly(L-lactide). V. Influence of Secondary Structure on the Mechanical Properties and Hydrolyzability of Poly(L-lactide) Fibers Produced by a Dry-Spinning Method", Journal of Applied Polymer Science, vol. 29, 1984, pp. 2829-2842.
Mezghani, "High Speed Melt Spinning of Poly(L-lactic acid) Filaments", Journal of Polymer Science, Part B: Polymer Physics, 1998, vol. 36,pp. 1005-1012.
Narayanan, Nonwovens Conference and Trade Fair, TAPPI Proceedings,"Dimensional Stability of Melt Blown Polyester Nonwovens", Mar. 9-11, 1998, pp. 29-36.
Resconi, "Selectivity in Propene Polymerization with Metallocene Catalysts" Chem. Rev., Mar. 25, 2000, vol. 100, pp. 1253-1345.
Scheirs, "Metallocene-based Polyolefins", vol. 1 and "Polyolefins", vol. 2, 2000, Wiley & Sons, Chichester, England, 10 pages.
Schmack, "High-Speed Melt Spinning of Various Grades of Polylactides", Journal of Applied Polymer Science,2004, vol. 91, pp. 800-806.
Solarski, "Characterization of the thermal properties of PLA fibers by modulated differential scanning calorimetry", Polymer, 2005, vol. 46, No. 25, pp. 11187-11192.
Takasaki, "Structural Development of Polylactides with Various d-Lactide contents in the High-Speed Melt Spinning Process", Journal of Macromolecular Science, Part B-Physics, 2003, vol. B42, No. 1, pp. 57-73.
Tsuji, "Stereocomplex formation between enantiomeric poly(lactic acid)s. XI. Mechanical properties and morphology of solution-cast films", Polymer, 1999, vol. 40, pp. 6699-6708.
Wente, "Manufacture of Superfine Organic Fibers", Report No. 4364 of the Naval Research Laboratories, Washington, D.C., .May 25, 1954, 22 pages.
Wente, "Superfine Thermoplastic Fibers", Industrial and Engineering Chemistry, 1956, vol. 48, pp. 1342-1346.
Ziabicki, "Fundamentals of Fibre Formation: The Science of Fibre Spinning and Drawing", John Wiley & Sons, 1976, 3 pages.
International Search Report, PCT/US2009/047064, dated Aug. 25, 2009, 5 pages.
International Search Report, PCT/US2010/028263, dated Dec. 3, 2010, 4 pages.
International Search Report, PCT/US2010/60951, dated Feb. 11, 2011, 11 pages.
International Search Report, PCT/US2010/60957, dated Feb. 28, 2011, 6 pages.
PCT/US2011/056257 application, filed Oct. 14, 2011, entitled Dimensionally Stable Nonwoven Fibrous Webs, and Methods of Making and Using the Same.
Wikipedia.com, Surfactant, http://en.wikipedia.org/wiki/Surfactant, copyright 2014; (11 pgs).
Silver Fern Chemical, Calcium Stearate, http://www.silverfernchemical.com/products/calcium-stearate, copyright 2014. (3 pgs).
Derwent Publication XP-002065130; vol. 40, No. 94; 1995; re: JP6248551 (1 pg).
Ellison, C.J. et al.; "Melt blown nanofibers: Fiber diameter distributions and onset of fiber breakup"; Polymer; vol. 48; 2007; pp. 3306-3316.
U.S. Appl. No. 62/069,934, filed Oct. 29, 2014, Chakravarty et al.
European Search Report for EP 17 17 7192 dated Nov. 16, 2017.

* cited by examiner

BIOCOMPATIBLE HYDROPHILIC COMPOSITIONS

CROSS REFERENCE TO RELATED APPLICATIONS

This application is a continuation of U.S. patent application Ser. No. 12/997,398, filed Mar. 4, 2011, (now allowed), which is a national stage filing under 35 U.S.C. 371 of PCT/US2009/047057, filed Jun. 11, 2009, which claims priority to U.S. Provisional Patent Application No. 61/061,088, filed Jun. 12, 2008, the disclosure of which is incorporated by reference in their entirety herein.

BACKGROUND

Thermoplastic polymers are widely employed to create a variety of products, including blown and cast films, extruded sheets, foams, fibers and products made therefrom, woven and knitted fabrics, and non-woven fibrous webs. Traditionally, many of these articles have been made from petroleum-based thermoplastics such as polyolefins.

There is a growing interest in replacing these petroleum based polymers with resource renewable polymers, i.e. polymers derived from plant based materials. Ideal resource renewable polymers are "carbon dioxide neutral" meaning that as much carbon dioxide is consumed in growing the plant based material as is given off when the product is made and disposed of. Biodegradable materials have adequate properties to permit them to break down when exposed to conditions which lead to composting. Examples of materials thought to be biodegradable include aliphatic polyesters such as poly(lactic acid), poly(glycolic acid), poly(caprolactone), copolymers of lactide and glycolide, poly(ethylene succinate), polybutylene succinate), polyhydroxybutyrate, and combinations thereof.

Degradation of aliphatic polyesters can occur through multiple mechanisms including hydrolysis, transesterification, chain scission, and the like. Instability of such polymers during processing can occur at elevated temperatures as described in WO 94/07941 (Gruber et al.).

The processing of aliphatic polyesters as microfibers has been described in U.S. Pat. No. 6,645,618. U.S. Pat. No. 6,111,160 (Gruber et al.) discloses the use of melt stable polylactides to form nonwoven articles via melt blown and spunbound processes.

Many thermoplastic polymers used in these products, such as polyhydroxyalkanoates (PHA), are inherently hydrophobic. That is, as a woven, knit, or nonwoven such as a spunbond fabric, they will not absorb water. There are a number of uses for thermoplastic polymers where their hydrophobic nature either limits their use or requires some effort to modify the surface of the shaped articles made therefrom. For example, polylactic acid has been reported to be used in the manufacture of nonwoven webs that are employed in the construction of absorbent articles such as diapers, feminine care products, and personal incontinence products (U.S. Pat. No. 5,910,368). These materials were rendered hydrophilic through the use of a post treatment topical application of a silicone copolyol surfactant. Such surfactants are not thermally stable and can break down in an extruder to yield formaldehyde.

U.S. Pat. No. 7,623,339 discloses a polyolefin resin rendered antimicrobial and hydrophilic using a combination of fatty acid monoglycerides and enhancer(s).

Coating methods to provide a hydrophilic surface are known, but also have some limitations. First of all, the extra step required in coating preparation is expensive and time consuming. Many of the solvents used for coating are flammable liquids or have exposure limits that require special production facilities. The quantity of surfactant can also be limited by the solubility of the surfactant in the coating solvent and the thickness of the coating.

Post treatment of the thermoplastic polymer can be undesirable for at least two other reasons. First, it can be more expensive since it requires additional processing steps of surfactant application and drying. Second, PHAs are polyesters, and thus prone to hydrolysis. It is desirable to limit the exposure of PHA polymers to water which can be present in the surfactant application solution. Furthermore, the subsequent drying step at elevated temperature in the wet web is highly undesirable.

DISCLOSURE OF INVENTION

The present disclosure is directed to a composition, article and method for making a durable hydrophilic and preferably biocompatible composition. The inventive compositions may be melt-processable and have utility in a variety of food safety, medical and water purification applications.

Exemplary aliphatic thermoplastic polyesters are poly (lactic acid), poly(glycolic acid), poly(lactic-co-glycolic acid), polyhydroxybutyrate, polyhydroxyvalerate, blends, and copolymers thereof. Blends may be made using a variety of other polymers including aromatic polyesters, aliphatic/aromatic copolyesters such as those described in U.S. Pat. No. 7,241,838 which is incorporated herein by reference, cellulose esters, cellulose ethers, thermoplastic starches, ethylene vinyl acetate, polyvinyl alcohol, ethylenevinyl alcohol, and the like. In blended compositions which include thermoplastic polymers which are not aliphatic polyesters, the aliphatic polyester is typically present at a concentration of greater than 60% by weight of total thermoplastic polymer, preferably greater than 70% by weight of total thermoplastic polymer and most preferably greater than about 75% by weight of thermoplastic polymer.

Inventive articles comprise molded polymeric articles, polymeric sheets, polymeric fibers, woven webs, nonwoven webs, porous membranes, polymeric foams, as well as layered compositions such as thermal or adhesive laminates, and combinations thereof made of the compositions described above. Examples of useful articles of this disclosure are wound contact materials made of a film, foam and/or woven or nonwoven comprising the inventive composition and surgical drapes or surgical gowns, as well as personal hygiene articles such as diapers, feminine hygiene pads and the like made of the inventive composition.

The method of the present disclosure comprises providing the aliphatic thermoplastic polyester and the surfactants as described herein, and mixing these materials sufficiently to yield a biocompatible, durable hydrophilic composition.

In one aspect, the polymer composition is melt processable, such that the polymer is capable of being extruded.

In another aspect, the polymer is solvent soluble or dispersible and the composition may be solvent cast, solvent spun to form films or fibers, or foams.

The melt processable composition of aliphatic polyesters and surfactants exhibit durable hydrophilicity. In some cases the surfactant may be dissolved in or along with a surfactant carrier. The surfactant carrier and/or surfactant may be a plasticizer for the thermoplastic aliphatic polyester. The plasticized aliphatic polyester generally has a lower melt processing temperature and can yield a more flexible output material.

For the following defined terms, these definitions shall be applied, unless a different definition is given in the claims or elsewhere in the specification.

The term "biodegradable" means degradable by the action of naturally occurring microorganisms such as bacteria, fungi and algae and/or natural environmental factors such as hydrolysis, transesterification, exposure to ultraviolet or visible light (photodegradable) and enzymatic mechanisms or combinations thereof.

The term "biocompatible" means biologically compatible by not producing toxic, injurious or immunological response in living tissue. Biocompatible materials may also be broken down by biochemical and/or hydrolytic processes and absorbed by living tissue. Test methods used include ASTM F719 for applications where the compositions contact tissue such as skin, wounds, mucosal tissue including in an orifice such as the esophagus or urethra, and ASTM F763 for applications where the compositions are implanted in tissue.

The term "durable hydrophilic" means that the composition, typically in fiber or fabric form, remains water absorbent when aged at least 30 days at 23° C. and preferably at least 40 days at 23° C.

The recitation of numerical ranges by endpoints includes all numbers subsumed within that range (e.g. 1 to 5 includes 1, 1.5, 2, 2.75, 3, 3.8, 4, and 5).

As used in this specification and the appended claims, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities or ingredients, measurement of properties and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques.

DETAILED DESCRIPTION

The present invention discloses the use of melt additive anionic surfactants, optionally combined with surfactant carriers such as polyethylene glycol, to impart stable durable hydrophilicity to aliphatic polyester thermoplastics such as polyhydroxyalkanoates (e.g. polylactic acid). This invention is particularly useful for making hydrophilic absorbent polylactic acid nonwoven/film laminate drapes used in surgery as well as personal care absorbents such as feminine hygiene pads, diapers, incontinence pads, and the like.

Hydrophilicity, or the lack thereof, can be measured in a variety of ways. For example, when water contacts a porous nonwoven web that is hydrophobic or has lost its hydrophilicity, the water does not flow, or flows undesirably slowly, through the web. Importantly the fibers and webs of the present invention exhibit stable hydrophilicity (water absorbency). That is, they remain hydrophilic after aging in a clean but porous enclosure such as a poly/Tyvek pouch for over 30 days at 23° C. or lower and preferably for over 40 days.

Preferred materials of this invention wet with water and thus have an apparent surface energy of great than 72 dynes/cm (surface tension of pure water). The most preferred materials of this invention instantly absorb water and remain water absorbent after aging for 10 days at 5° C., 23° C. and 45° C. More preferred materials of this invention instantly absorb water and remain water absorbent after aging for 20 days at 5° C., 23° C. and 45° C. Even more materials of this invention instantly absorb water and remain water absorbent after aging for 30 days at 5° C., 23° C. and 45° C.

Most preferred compositions remain hydrophilic (water absorbent) after more than 10 days at 45° C., preferably more than 30 days and most preferably greater than 40 days, when tested according to the methods described in the Examples. The preferred fabrics are instantaneously wettable and absorbent and are capable of absorbing water at very high initial rates.

In one aspect, this invention provides a durable hydrophilic, thermoplastic composition comprising at least one thermoplastic aliphatic polyester polymer, e.g., polylactic acid, polyhydroxybutyrate and the like, and one or more surfactants selected from the group of alkyl, alkaryl, alkenyl or aralkyl sulfate; alkyl, alkaryl, alkenyl or aralkyl sulfonate; alkyl, alkaryl, alkenyl or aralkyl carboxylate; or alkyl, alkaryl, alkenyl or aralkyl phosphate surfactants. The compositions may optionally comprise a surfactant carrier which may aid processing and/or enhance the hydrophilic properties. The blend of the surfactant(s) and optionally a surfactant carrier is present in the melt extruded fiber in an amount sufficient to impart durable hydrophilicity to the fiber at its surface.

Preferably the surfactant is soluble in the carrier at extrusion temperatures at the concentrations used. Solubility can be evaluated, for example, as the surfactant and carrier form a visually transparent solution in a 1 cm path length glass vial when heated to extrusion temperature (e.g. 150-190° C.). Preferably the surfactant is soluble in the carrier at 150° C. More preferably the surfactant is soluble in the carrier at less than 100° C. so that it can be more easily incorporated into the polymer melt. More preferably the surfactant is soluble in the carrier at 25° C. so that no heating is necessary when pumping the solution into the polymer melt.

Preferably the surfactant is soluble in the carrier at greater than 10% by weight, more preferably greater than 20% by weight, and most preferably greater than 30% by weight in order to allow addition of the surfactant without too much carrier present, which may plasticize the thermoplastic. Typically the surfactants are present at present in a total amount of at least 0.25 wt-%, preferably at least 0.50 wt-%, more preferably at least 0.75 wt-%, based on the total weight of the composition. In certain embodiments, in which a very hydrophilic web is desired, or a web that can withstand multiple assaults with aqueous fluid, the surfactant component comprises greater than 2 wt. %, greater than 3 wt. %, or even greater than 5 wt. % of the degradable aliphatic polyester polymer composition. In certain embodiments, the surfactants typically are present at 0.25 wt. % to 8 wt. % of the degradable aliphatic polyester polymer composition.

The surfactant and optional carrier should be relatively free of moisture in order to facilitate extrusion and to prevent hydrolysis of the aliphatic polyester. Preferably the surfactant and optional carrier, either alone or in combination, comprise less than 5% water, more preferably less than 2% water, even more preferably less than 1% water, and most preferably less than 0.5% water by weight as determined by a Karl-Fisher titration.

In another aspect, the present invention provides durable hydrophilic films and durable hydrophilic fabrics and webs constructed from said fibers. The invention also provides useful articles made from durable hydrophilic fabrics and webs including medical drapes, wound dressings, medical gowns, aprons, filter media, industrial wipes and personal care and home care products such as diapers, facial tissue, facial wipes, wet wipes, dry wipes, disposable absorbent articles and garments such as infant diapers or training pants, adult incontinence products, feminine hygiene products such as sanitary napkins and panty liners and the like. The invention also provides useful antifog films when using transparent aliphatic polyesters. These antifog films may be used in food packaging, for safety eyewear and the like.

In yet another aspect, this invention provides multi-layer, aqueous liquid-absorbent articles comprising an aqueous media impervious backing sheet. For example, importantly some surgical drapes are liquid impervious to prevent liquid that is absorbed into the top sheet from wicking through to the skin surface where it would be contaminated with bacteria present on the skin. In other embodiments the construction may further comprise an aqueous media permeable topsheet, and an aqueous liquid-absorbent (i.e., hydrophilic) layer constructed of the above-described web or fabric juxtaposed there between, useful in constructing for example, disposable diapers, wipes or towels, sanitary napkins, and incontinence pads.

The compositions of this invention are "relatively homogenous". That is, the compositions can be produced by melt extrusion with good mixing and at the time of extrusion would be relatively homogenous in concentration throughout. It is recognized, however, that over time and/or with heat treatment the surfactant(s) may migrate to become higher or lower in concentration at certain points, such as at the surface of the fiber.

In another aspect, a method of preparing durable hydrophilic fibers from a mixture or blend of thermoplastic film-forming aliphatic polyester, and at least one surfactant, is provided. The melt of the blend is processed or shaped, for example, by extrusion or molding to produce fibers with the surfactants dissolved or dispersed within the fiber and present at the surfaces of the fiber to render those surfaces durably hydrophilic. Because some surfactants demonstrate thermal sensitivity, the processing temperatures in the extruder are preferably kept below about 300° C., more preferably below about 250° C., and even more preferably below 200° C. where those surfactants are exposed to such temperatures given the particular processing technique. The durable hydrophilicity is achieved without requiring post fiber finishing operations, e.g. application of additional surfactant, because the fiber is durably hydrophilic as extruded, however, heating the web after extrusion may help to bloom surfactant to the surface and improve hydrophilicity. This is done at temperatures at or above the glass transition temperature of the thermoplastic(s) and is typically less than 120° C. and even less than 100° C.

The hydrophilicity imparted to the fiber compositions described herein is done using at least one melt additive surfactant. Suitable anionic surfactants include alkyl, alkenyl, alkaryl, or aralkyl sulfate, alkyl, alkenyl, alkaryl, or aralkyl sulfonate, alkyl, alkenyl alkaryl, or aralkyl phosphate, alkyl, alkenyl, alkaryl, or aralkyl carboxylate or a combination thereof. The alkyl and alkenyl groups may be linear or branched. These surfactants may be modified as is known in the art. For example, as used herein an "alkyl carboxylate" is a surfactant having an alkyl group and a carboxylate group but it may also include, for example, bridging moieties such as polyalkylene oxide groups, e.g., isodeceth-7 carboxylate sodium salt is an alkyl carboxylate having a branched chain of ten carbons (C10) alkyl group, seven moles of ethylene oxide and terminated in a carboxylate.

The surfactants of this invention can be conveniently compounded with the resin in a concentrate (masterbatch) composition, which can then mixed be with the virgin thermoplastic polymer in the hopper or elsewhere along the extruder as long as blending is achieved to render a substantially uniform mixture. Alternatively, the surfactant may be added as into the extruder directly (without precompounding), for example, using a positive displacement pump or weight loss feeder. This is most conveniently done if the surfactant is dissolved or dispersed in a surfactant carrier such as a polyalkylene oxide or polyol.

Certain classes of hydrocarbon, silicone, and fluorochemical surfactants have each been described as useful for imparting hydrophilicity to polyolefins. These surfactants typically are contacted with the thermoplastic resin in one of two ways: (1) by topical application, e.g., spraying or padding or foaming, of the surfactants from aqueous solution to the extruded nonwoven web or fiber followed by drying, or (2) by incorporation of the surfactant into the polyolefin melt prior to extrusion of the web. The latter is much preferable but is difficult to find a surfactant that will spontaneously bloom to the surface of the fiber or film in sufficient amount to render the article hydrophilic. As previously described, webs made hydrophilic by topical application of a surfactant suffer many drawbacks. Some are reported to also have diminished hydrophilicity after a single contact with aqueous media. Additional disadvantages to topical application of a surfactant to impart hydrophilicity may include skin irritation from the surfactant itself, non-uniform surface and bulk hydrophilicity, and the additive cost resulting from the necessity of an added processing step in the surfactant application. Incorporating one or more surfactants into to the thermoplastic polymer as a melt additive alleviates the problems associated with topical application and in addition may provide a softer "hand" to the fabric or nonwoven web into which it is incorporated. The challenge as previously stated, is finding a surfactant that will reliably bloom to the surface of the article in sufficient amount to impart hydrophilicity and then to remain properly oriented at the surface to ensure durable hydrophilicity.

The fibers described herein remain hydrophilic and water absorbent after repeated insult with water, e.g. saturating with water, wringing out and allowing to dry. Preferred compositions of this invention include a relatively homogenous composition comprising at least one aliphatic polyester resin (preferably polylactic acid), at least one alkylsulfate, alkylene sulfate, or aralkyl or alkaryl sulfate, carboxylate, or phosphate surfactant, typically in an amount of at 0.25 wt % to 8 wt %, and optionally a nonvolatile carrier in a concentration of 1 wt % to 8 wt %, as described in more detail below.

Preferred porous fabric constructions of the present invention produced as knits, wovens, and nonwovens have apparent surface energies greater than 60 dynes/cm, and preferably greater than 70 dynes/cm when tested by the Apparent Surface Energy Test disclosed in the Examples. Preferred porous fabric materials of this invention wet with water and thus have an apparent surface energy of greater than 72 dynes/cm (surface tension of pure water). The most preferred materials of this invention instantly absorb water and remain water absorbent after aging for 10 days at 5° C., 23° C. and 45° C. "Instant" absorption means a 25 µl drop of water that is gently placed on the fabric does not form a discrete droplet on the surface of the fabric but is absorbed into the pores.

Preferred film constructions of the present invention are wettable by aqueous fluids and have a contact angle with deionized water of less than 40 degrees, preferably less than 30 degrees, and most preferably less than 20 degrees when measured using a Tantec Contact Angle Meter (Shaumburg, Ill.), described as the half-angle technique in U.S. Pat. No. 5,268,733.

The present invention also discloses a method of making a relatively homogenous hydrophilic aliphatic polyester composition comprising an anionic surfactant and optionally a surfactant carrier by blending these in a melt process, and forming a film, fiber, or foam.

The present invention also discloses a method of making a relatively homogenous hydrophilic aliphatic polyester composition comprising an anionic surfactant and optionally a surfactant carrier by blending these to form a concentrate, blending the concentrate with additional aliphatic polyester in a melt process, and forming a film, fiber, or foam.

The present invention also discloses a method of making a relatively homogenous hydrophilic aliphatic polyester composition comprising an anionic surfactant and optionally a surfactant carrier by blending these in a melt process, forming a film, fiber, or foam, and post heating the film, fiber or foam to a temperature greater than 50° C.

The present invention also discloses a method of making a relatively homogenous hydrophilic aliphatic polyester composition comprising an anionic surfactant and optionally a surfactant carrier by blending these to form a concentrate, blending the concentrate with additional aliphatic polyester in a melt process, forming a film, fiber, or foam and post heating the film, fiber, or foam to a temperature greater than 50° C.

Polyesters

Aliphatic polyesters useful in the present invention include homo- and copolymers of poly(hydroxyalkanoates), and homo- and copolymers of those aliphatic polyesters derived from the reaction product of one or more polyols with one or more polycarboxylic acids that are typically formed from the reaction product of one or more alkanediols with one or more alkanedicarboxylic acids (or acyl derivatives). Polyesters may further be derived from multifunctional polyols, e.g. glycerin, sorbitol, pentaerythritol, and combinations thereof, to form branched, star, and graft homo- and copolymers. Polyhydroxyalkanoates generally are formed from hydroxyacid monomeric units or derivatives thereof. These include, for example, polylactic acid, polyhydroxybutyrate, polyhydroxyvalerate, polycaprolactone and the like. Miscible and immiscible blends of aliphatic polyesters with one or more additional semicrystalline or amorphous polymers may also be used.

One useful class of aliphatic polyesters are poly(hydroxyalkanoates), derived by condensation or ring-opening polymerization of hydroxy acids, or derivatives thereof. Suitable poly(hydroxyalkanoates) may be represented by the formula:

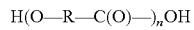

H(O—R—C(O)—)$_n$OH where R is an alkylene moiety that may be linear or branched having 1 to 20 carbon atoms, preferably 1 to 12 carbon atoms optionally substituted by catenary (bonded to carbon atoms in a carbon chain) oxygen atoms; n is a number such that the ester is polymeric, and is preferably a number such that the molecular weight of the aliphatic polyester is at least 10,000, preferably at least 30,000, and most preferably at least 50,000 daltons. Although higher molecular weight polymers generally yield films and fibers with better mechanical properties, for both melt processed and solvent cast polymers, excessive viscosity is typically undesirable. It is a significant advantage of the present invention that the surfactant carrier and/or surfactant component in many embodiments plasticizes the polyester component allowing for melt processing and solvent casting of higher molecular weight polymers. Thus, the molecular weight of the aliphatic polyester is typically less than 1,000,000, preferably less than 500,000, and most preferably less than 300,000 daltons. R may further comprise one or more caternary (i.e. in chain) ether oxygen atoms. Generally, the R group of the hydroxy acid is such that the pendant hydroxyl group is a primary or secondary hydroxyl group.

Useful poly(hydroxyalkanoates) include, for example, homo- and copolymers of poly(3-hydroxybutyrate), poly(4-hydroxybutyrate), poly(3-hydroxyvalerate), poly(lactic acid) (as known as polylactide), poly(3-hydroxypropanoate), poly(4-hydropentanoate), poly(3-hydroxypentanoate), poly(3-hydroxyhexanoate), poly(3-hydroxyheptanoate), poly(3-hydroxyoctanoate), polydioxanone, polycaprolactone, and polyglycolic acid (i.e. polyglycolide). Copolymers of two or more of the above hydroxy acids may also be used, for example, poly(3-hydroxybutyrate-co-3-hydroxyvalerate), poly(lactate-co-3-hydroxypropanoate), poly(glycolide-co-p-dioxanone), and poly(lactic acid-co-glycolic acid). Blends of two or more of the poly(hydroxyalkanoates) may also be used, as well as blends with one or more semicrystalline or amorphous polymers and/or copolymers.

The aliphatic polyester may be a block copolymer of poly(lactic acid-co-glycolic acid). Aliphatic polyesters useful in the inventive compositions may include homopolymers, random copolymers, block copolymers, star-branched random copolymers, star-branched block copolymers, dendritic copolymers, hyperbranched copolymers, graft copolymers, and combinations thereof.

Another useful class of aliphatic polyesters includes those aliphatic polyesters derived from the reaction product of one or more alkanediols with one or more alkanedicarboxylic acids (or acyl derivatives). Such polyesters have the general formula:

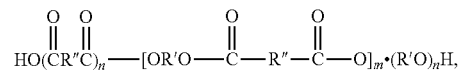

$$HO(CR''C)_n\text{—}[OR'O\text{—}\overset{O}{\underset{\|}{C}}\text{—}R''\text{—}\overset{O}{\underset{\|}{C}}\text{—}O]_m\text{•}(R'O)_nH,$$

where R' and R" each represent an alkylene moiety that may be linear or branched having from 1 to 20 carbon atoms, preferably 1 to 12 carbon atoms, and m is a number such that the ester is polymeric, and is preferably a number such that the molecular weight of the aliphatic polyester is at least 10,000, preferably at least 30,000, and most preferably at least 50,000 daltons, but less than 1,000,000, preferably less than 500,000 and most preferably less than 300,000 daltons. Each n is independently 0 or 1. R' and R" may further comprise one or more caternary (i.e. in chain) ether oxygen atoms.

Examples of aliphatic polyesters include those homo- and copolymers derived from (a) one or more of the following diacids (or derivative thereof): succinic acid; adipic acid; 1,12 dicarboxydodecane; fumaric acid; glutartic acid; diglycolic acid; and maleic acid; and (b) one of more of the following diols: ethylene glycol; polyethylene glycol; 1,2-propane diol; 1,3-propanediol; 1,2-propanediol; 1,2-butanediol; 1,3-butanediol; 1,4-butanediol; 2,3-butanediol; 1,6-hexanediol; 1,2 alkane diols having 5 to 12 carbon atoms; diethylene glycol; polyethylene glycols having a molecular weight of 300 to 10,000 daltons, and preferably 400 to 8,000 daltons; propylene glycols having a molecular weight of 300 to 4000 daltons; block or random copolymers derived from ethylene oxide, propylene oxide, or butylene oxide; dipropylene glycol; and polypropylene glycol, and (c) optionally a small amount, i.e., 0.5-7.0 mole percent of a polyol with a functionality greater than two, such as glycerol, neopentyl glycol, and pentaerythritol.

Such polymers may include polybutylene succinate homopolymer, polybutylene adipate homopolymer, polybutyleneadipate-succinate copolymer, polyethylenesuccinate-adipate copolymer, polyethylene glycol succinate homopolymer and polyethylene adipate homopolymer.

Commercially available aliphatic polyesters include poly (lactide), poly(glycolide), poly(lactide-co-glycolide), poly (L-lactide-co-trimethylene carbonate), poly(dioxanone), poly(butylene succinate), and poly(butylene adipate).

Useful aliphatic polyesters include those derived from semicrystalline polylactic acid. Poly(lactic acid) or polylactide has lactic acid as its principle degradation product, which is commonly found in nature, is non-toxic and is widely used in the food, pharmaceutical and medical industries. The polymer may be prepared by ring-opening polymerization of the lactic acid dimer, lactide. Lactic acid is optically active and the dimer appears in four different forms: L,L-lactide, D,D-lactide, D,L-lactide (meso lactide) and a racemic mixture of L,L- and D,D-. By polymerizing these lactides as pure compounds or as blends, poly(lactide) polymers may be obtained having different stereochemistries and different physical properties, including crystallinity. The L,L- or D,D-lactide yields semicrystalline poly (lactide), while the poly(lactide) derived from the D,L-lactide is amorphous.

The polylactide preferably has a high enantiomeric ratio to maximize the intrinsic crystallinity of the polymer. The degree of crystallinity of a poly(lactic acid) is based on the regularity of the polymer backbone and the ability to crystallize with other polymer chains. If relatively small amounts of one enantiomer (such as D-) is copolymerized with the opposite enantiomer (such as L-) the polymer chain becomes irregularly shaped, and becomes less crystalline. For these reasons, when crystallinity is favored, it is desirable to have a poly(lactic acid) that is at least 85% of one isomer, at least 90% of one isomer, or at least 95% of one isomer in order to maximize the crystallinity.

An approximately equimolar blend of D-polylactide and L-polylactide is also useful. This blend forms a unique crystal structure having a higher melting point (~210° C.) than does either the D-poly(lactide) and L-(polylactide) alone (~190° C.), and has improved thermal stability. See H. Tsuji et al., *Polymer,* 40 (1999) 6699-6708.

Copolymers, including block and random copolymers, of poly(lactic acid) with other aliphatic polyesters may also be used. Useful co-monomers include glycolide, beta-propiolactone, tetramethylglycolide, beta-butyrolactone, gamma-butyrolactone, pivalolactone, 2-hydroxybutyric acid, alpha-hydroxyisobutyric acid, alpha-hydroxyvaleric acid, alpha-hydroxyisovaleric acid, alpha-hydroxycaproic acid, alpha-hydroxyethylbutyric acid, alpha-hydroxyisocaproic acid, alpha-hydroxy-beta-methylvaleric acid, alpha-hydroxyoctanoic acid, alpha-hydroxydecanoic acid, alpha-hydroxymyristic acid, and alpha-hydroxystearic acid.

Blends of poly(lactic acid) and one or more other aliphatic polyesters, or one or more other polymers may also be used. Examples of useful blends include poly(lactic acid) and poly(vinyl alcohol), polyethylene glycol/polysuccinate, polyethylene oxide, polycaprolactone and polyglycolide.

Poly(lactide)s may be prepared as described in U.S. Pat. No. 6,111,060 (Gruber, et al.), U.S. Pat. No. 5,997,568 (Liu), U.S. Pat. No. 4,744,365 (Kaplan et al.), U.S. Pat. No. 5,475,063 (Kaplan et al.), U.S. Pat. No. 6,143,863 (Gruber et al.), U.S. Pat. No. 6,093,792 (Gross et al.), U.S. Pat. No. 6,075,118 (Wang et al.), U.S. Pat. No. 5,952,433 (Wang et al.), WO 98/24951 (Tsai et al.), WO 00/12606 (Tsai et al.), WO 84/04311 (Lin), U.S. Pat. No. 6,117,928 (Hiltunen et al.), U.S. Pat. No. 5,883,199 (McCarthy et al.), WO 99/50345 (Kolstad et al.), WO 99/06456 (Wang et al.), WO 94/07949 (Gruber et al.), WO 96/22330 (Randall et al.), and WO 98/50611 (Ryan et al.), the disclosure of each incorporated herein by reference. Reference may also be made to J. W. Leenslag, et al., *J. Appl. Polymer Science*, vol. 29 (1984), pp 2829-2842, and H. R. Kricheldorf, *Chemosphere*, vol. 43, (2001) 49-54.

The molecular weight of the polymer should be chosen so that the polymer may be processed as a melt or cast from a solvent. For polylactide, for example, the molecular weight may be from about 10,000 to 1,000,000 daltons, and is preferably from about 30,000 to 300,000 daltons. By "melt-processable", it is meant that the aliphatic polyesters are fluid or can be pumped or extruded at the temperatures used to process the articles (e.g. films), and do not degrade or gel at those temperatures to the extent that the physical properties are so poor as to be unusable for the intended application. Thus, many of the materials described herein may be made into films by extrusion, casting, thermal pressing, and the like. They can be made into nonwovens using melt processes such as spunbond, blown microfiber, melt spinning and the like. Certain embodiments also may be injection molded. Generally, weight average molecular weight ($M_w$) of the polymers is above the entanglement molecular weight, as determined by a log-log plot of viscosity versus number average molecular weight ($M_n$). Above the entanglement molecular weight, the slope of the plot is about 3.4, whereas the slope of lower molecular weight polymers is 1.

The aliphatic polyester component of the composition typically comprises at least 60 weight percent, preferably at least 70 weight percent, and most preferably at least 75 weight percent, based on the total weight of the durable hydrophilic composition.

Surfactants

Compositions of the present invention include one or more surfactants to help wet the surface and/or to aid in contacting and killing microorganisms. As used herein the term "surfactant" means an amphiphile (a molecule possessing both polar and nonpolar regions which are covalently bound) capable of reducing the surface tension of water and/or the interfacial tension between water and an immiscible liquid. The term is meant to include soaps, detergents, emulsifiers, surface active agents, and the like.

In applications in which biodegradability is important, it may be desirable to incorporate biodegradable surfactants, which typically include ester and/or amide groups that may be hydrolytically or enzymatically cleaved. In certain preferred embodiments, the surfactants useful in the compositions of the present invention are anionic surfactants selected from the group consisting of alkyl, alkenyl, alkaryl and arakyl sulfonates, sulfates, phosphonates, phosphates and mixtures thereof. Included in these classes are alkylalkoxylated carboxylates, alkyl alkoxylated sulfates, alkylalkoxylated sulfonates, and alkyl alkoxylated phosphates, and mixtures thereof. The preferred alkoxylate is made using ethylene oxide and/or propylene oxide with 0-100 moles of ethylene and propylene oxide per mole of hydrophobe. In certain more preferred embodiments, the surfactants useful in the compositions of the present invention are selected from the group consisting of sulfonates, sulfates, phosphates, carboxylates and mixtures thereof. In one aspect, the surfactant is selected from (C8-C22) alkyl sulfate salts (e.g., sodium salt); di(C8-C13 alkyl)sulfosuccinate salts; C8-C22 alkyl sarconsinate; C8-C22 alkyl lactylates; and combinations thereof. Combinations of various surfactants can also be used.

The anionic surfactants useful in this invention are described in more detail below and include surfactants with the following structure:

$$R-(O)_xSO_3^-M^+ \text{ and } R-CO_2^-M^+$$

Where:
R=alkyl or alkylene of C8-C30, which is branched or straight chain, or C12-C30 aralkyl, and may be optionally substituted with 0-100 alkylene oxide groups such as ethylene oxide, propylene oxide groups, oligomeric lactic and/or glycolic acid or a combination thereof.
X=0 or 1
M=alkali metal salts, preferably Li+, K+, or Na+, or amine salts including tertiary and quaternary amines.

Examples include C8-C18 alkane sulfonates; C8-C18 secondary alkane sulfonates; alkylbenzene sulfonates such as dodecylbenzene sulfonate; C8-C18 alkyl sulfates; alkylether sulfates such as sodium trideceth-4 sulfate, sodium laureth 4 sulfate, sodium laureth 8 sulfate (such as those available from Stepan Company, Northfield Ill.), docusate sodium also known as dioctylsulfosuccinate, sodium salt; lauroyl lacylate and stearoyl lactylate (such as those available from RITA Corporation, Crystal Lake, Ill. under the PATIONIC tradename), and the like.

Surfactants with the following structure can also be useful:

$$(R-O)_2P(O)O^-M^+ \text{ or } R-OP(O)(O^-)_2M^+_2$$

Where R and M are defined above. Examples include stearyl phosphate (available as Sippostat 0018 from Specialty Industrial Products, Inc., Spartanburg, S.C.); Cetheth-10 PPG-5 phosphate (Crodaphos SG, available from Croda USA, Edison N.J.); laureth-4 phosphate; and dilaureth-4 phosphate.

Exemplary anionic surfactants include, but are not limited to, sarcosinates, glutamates, alkyl sulfates, sodium or potassium alkyleth sulfates, ammonium alkyleth sulfates, ammonium laureth-n-sulfates, laureth-n-sulfates, isethionates, glycerylether sulfonates, sulfosuccinates, alkylglyceryl ether sulfonates, alkyl phosphates, aralkyl phosphates, alkylphosphonates, and aralkylphosphonates. These anionic surfactants may have a metal or organic ammonium counterion. Certain useful anionic surfactants are selected from the group consisting of: sulfonates and sulfates such as alkyl sulfates, alkylether sulfates, alkyl sulfonates, alkylether sulfonates, alkylbenzene sulfonates, alkylbenzene ether sulfates, alkylsulfoacetates, secondary alkane sulfonates, secondary alkylsulfates, and the like. Many of these can be represented by the formulas:

$$R^{26}-(OCH_2CH_2)_{n6}(OCH(CH_3)CH_2)_{p2}-(Ph)_a-(OCH_2CH_2)_{m3}(O)_b-SO_3^-M^+$$

and $$R^{26}-CH[SO_3^-M^+]-R^{27}$$

wherein: a and b=0 or 1; n6, p2, and m3=0-100 (preferably 0-20); $R^{26}$ is defined as below provided at least one $R^{26}$ or $R^{27}$ is at least C8; $R^{27}$ is a (C1-C12)alkyl group (saturated straight, branched, or cyclic group) that may be optionally substituted by N, O, or S atoms or hydroxyl, carboxyl, amide, or amine groups; Ph=phenyl; and M is a cationic counterion such as H, Na, K, Li, ammonium, or a protonated tertiary amine such as triethanolamine or a quaternary ammonium group.

In the formula above, the ethylene oxide groups (i.e., the "n6" and "m3" groups) and propylene oxide groups (i.e., the "p2" groups) can occur in reverse order as well as in a random, sequential, or block arrangement. $R^{26}$ may be an alkylamide group such as $R^{28}-C(O)N(CH_3)CH_2CH_2-$ as well as ester groups such as $-OC(O)-CH_2-$ wherein $R^{28}$ is a (C8-C22)alkyl group (branched, straight, or cyclic group). Examples include, but are not limited to: alkyl ether sulfonates, including lauryl ether sulfates (such as POLY-STEP B12 (n=3-4, M=sodium) and B22 (n=12, M=ammonium) available from Stepan Company, Northfield, Ill.) and sodium methyl taurate (available under the trade designation NIKKOL CMT30, Nikko Chemicals Co., Tokyo, Japan); secondary alkane sulfonates, including sodium (C14-C17) secondary alkane sulfonates (alpha-olefin sulfonates) (such as Hostapur SAS available from Clariant Corp., Charlotte, N.C.); methyl-2-sulfoalkyl esters such as sodium methyl-2-sulfo(C12-16)ester and disodium 2-sulfo(C12-C16) fatty acid (available from Stepan Company, Northfield, Ill. under the trade designation ALPHASTEP PC-48); alkylsulfoacetates and alkylsulfosuccinates available as sodium laurylsulfoacetate (under the trade designation LANTHANOL LAL, Stepan Company, Northfield, Ill.) and disodiumlaurethsulfosuccinate (STEPANMILD SL3, Stepan Company, Northfield, Ill.); alkylsulfates such as ammoniumlauryl sulfate (available under the trade designation STEPANOL AM from Stepan Company, Northfield, Ill.); dialkylsulfosuccinates such as dioctylsodiumsulfosuccinate (available as Aerosol OT from Cytec Industries, Woodland Park, N.J.).

Suitable anionic surfactants also include phosphates such as alkyl phosphates, alkylether phosphates, aralkylphosphates, and aralkylether phosphates. Many may be represented by the formula:

$$[R^{26}\text{-}(Ph)_a\text{-}O(CH_2CH_2O)_{n6}(CH_2CH(CH_3)O)_{p2}]_{q2}\text{--}P(O)[O^-M^+]_r,$$

wherein: Ph, $R^{26}$, a, n6, p2, and M are defined above; r is 0-2; and q2=1-3; with the proviso that when q2=1, r=2, and when q2=2, r=1, and when q2=3, r=0. As above, the ethylene oxide groups (i.e., the "n6" groups) and propylene oxide groups (i.e., the "p2" groups) can occur in reverse order as well as in a random, sequential, or block arrangement. Examples include a mixture of mono-, di- and tri-(alkyltetraglycolether)-o-phosphoric acid esters generally referred to as trilaureth-4-phosphate (available under the trade designation HOSTAPHAT 340KL from Clariant Corp.); as well as PPG-5 ceteth 10 phosphate (available under the trade designation CRODAPHOS SG from Croda Inc., Parsipanny, N.J.), and mixtures thereof.

One or more surfactants may be used in and/or on the compositions described herein at a suitable level to produce the desired result. In some embodiments, when used in the composition, they are present in a total amount of at least 0.25 wt. %, at least 0.5 wt-%, at least 0.75 wt-%, at least 1.0 wt-%, or at least 2.0 wt-%, based on the total weight of the composition. In certain embodiments, in which a very hydrophilic web is desired, or a web that can withstand multiple assaults with aqueous fluid, the surfactant component comprises greater than 2 wt. %, greater than 3 wt. %, or even greater than 5 wt. % of the degradable aliphatic polyester polymer composition.

In other embodiments, the surfactants are present in a total amount of no greater than 20 wt. %, no greater than 15 wt. %, no greater than 10 wt. %, or no greater than 8 wt. %, based on the total weight of the ready to use composition.

Preferred surfactants have a melting point of less than 200° C., preferably less than 190° C., more preferably less than 180° C., and even more preferably less than 170° C.

For melt processing, preferred surfactant components have low volatility and do not decompose appreciably under process conditions. The preferred surfactants contain less than 10 wt. % water, preferably less than 5% water, and more preferably less than 2 wt. % and even more preferably less than 1% water (determined by Karl Fischer analysis). Moisture content is kept low in order to prevent hydrolysis of the aliphatic polyester or other hydrolytically sensitive compounds in the composition, which will help to give clarity to extruded films or fibers.

We have found that it is particularly convenient to use a surfactant predissolved in a non-volatile carrier. Importantly, the carrier is typically thermally stable and can resist chemical breakdown at processing temperatures which may be as high as 150° C., 180° C., 200° C. or even as high as 250° C. In a preferred embodiment, the surfactant carrier is a liquid at 23° C. Preferred carriers include polyalkylene oxides such as polyethylene glycol, polypropylene glycol, random and block copolymers of ethylene oxide and propylene oxide, thermally stable polyhydric alcohols such as propylene glycol, glycerin, polyglycerin, and the like. The polyalkylene oxides may be linear or branched depending on the initiating polyol. For example, a polyethylene glycol initiated using ethylene glycol would be linear but one initiated with glycerin, trimethylolpropane, or pentaerythritol would be branched.

Preferred carriers also may include low molecular weight esters of polyhydric alcohols such as triacetin, glyceryl caprylate/caprate, acetyltributylcitrate, and the like.

The solubilizing liquid carriers may alternatively be selected from non-volatile organic solvents. For purposes of the present invention, an organic solvent is considered to be nonvolatile if greater than 80% of the solvent remains in the composition throughout the mixing and melt processes. Because these liquids remain in the melt processable composition, they function as plasticizers, generally lowering the glass transition temperature of the composition.

Since the carrier is substantially nonvolatile it will in large part remain in the composition and may function as an organic plasticizer. As used herein a plasticizer is a compound having a molecular weight less than 1000 daltons which when added to the polymer composition results in a decrease in the glass transition temperature. Possible surfactant carriers include compounds containing one or more hydroxyl groups, and particularly glycols such glycerin; 1,2 pentanediol; 2,4 diethyl-1,5 pentanediol; 2-methyl-1,3-propanediol; as well as monofunctional compounds such 3-methoxy-methylbutanol ("MMB"). Additional examples of nonvolatile organic plasticizers include polyethers, including polyethoxylated phenols such as Pycal 94 (phenoxypolyethyleneglycol); alkyl, aryl, and aralkyl ether glycols (such as those sold under the Dowanol tradename by Dow Chemical Company, Midland Mich.) including but not limited to propylene glycolmonobutyl ether (Dowanol PnB), tripropyleneglycol monobutyl ether (Dowanol TPnB), dipropyeleneglycol monobutyl ether (Dowanol DPnB), propylene glycol monophenyl ether (Dowanol PPH), and propylene glycol monomethyl ether (Dowanol PM); polyethoxylated alkyl phenols such as Triton X35 and Triton X102 (available from Dow Chemical Company, Midland Mich.); mono or polysubstituted polyethylene glycols such as PEG 400 diethylhexanoate (TegMer 809, available from CP Hall Company), PEG 400 monolaurate (CHP-30N available from CP Hall Company) and PEG 400 monooleate (CPH-41N available from CP Hall Company); amides including higher alkyl substituted N-alkyl pyrrolidones such as N-octylpyrrolidone; sulfonamides such as N-butylbenzene sulfonamide (available from CP Hall Company); triglycerides; citrate esters; esters of tartaric acid; benzoate esters (such as those available from Velsicol Chemical Corp., Rosemont Ill. under the Benzoflex tradename) including dipropylene glycoldibenzoate (Benzoflex 50) and diethylene glycol dibenzoate; benzoic acid diester of 2,2,4 trimethyl 1,3 pentane diol (Benzoflex 354), ethylene glycol dibenzoate, tetraetheylene glycoldibenzoate, and the like; polyethylene glycols and ethylene oxide propylene oxide random and block copolymers having a molecular weight less than 10,000 daltons, preferably less than about 5000 daltons, more preferably less than about 2500 daltons; and combinations of the foregoing. As used herein the term polyethylene glycols refer to glycols having 26 alcohol groups that have been reacted with ethylene oxide or a 2 haloethanol.

Preferred polyethylene glycols are formed from ethylene glycol, propylene glycol, glycerin, trimethylolpropane, pentaerithritol, sucrose and the like. Most preferred polyethylene glycols are formed from ethylene glycol, propylene glycol, glycerin, and trimethylolpropane. Polyalkylene glycols such as polypropylene glycol, polytetramethylene glycol, or random or block copolymers of C2 C4 alkylene oxide groups may also be selected as the carrier. Polyethylene glycols and derivatives thereof are presently preferred. It is important that the carriers be compatible with the polymer. For example, it is presently preferred to use non-volatile non-polymerizable plasticizers that have less than 2 nucleophilic groups, such as hydroxyl groups, when blended with polymers having acid functionality, since compounds having more than two nucleophilic groups may result in crosslinking of the composition in the extruder at the high extrusion temperatures. Importantly, the non-volatile carriers preferably form a relatively homogeneous solution with the aliphatic polyester polymer composition in the extruder, and remain a relatively homogeneous composition upon cooling, such that the extruded composition is relatively uniform in surfactant concentration.

Optional Components

Other optional components may be included in the compositions described herein.

An antimicrobial component may be added to impart antimicrobial activity to the compositions. The antimicrobial component is that component of the composition that provides at least part of the antimicrobial activity, i.e., it has at least some antimicrobial activity for at least one microorganism. It is preferably present in a large enough quantity to be leached from the composition and kill bacteria. It may also be biodegradable and/or made or derived from renewable resources such as plants or plant products. Biodegradable antimicrobial components can include at least one functional linkage such as an ester or amide linkage that can be hydrolytically or enzymatically degraded.

Examples of antimicrobial components suitable for use in the present invention include those described in Applicants' co-pending application, U.S. Patent Application Publication No. 2008-0142023A1, incorporated by reference herein in its entirety.

Certain antimicrobial components are uncharged and have an alkyl or alkenyl hydrocarbon chain containing at least 7 carbon atoms. For melt processing, preferred antimicrobial components have low volatility and do not decompose under process conditions. The preferred antimicrobial components contain less than 2 wt. % water, and more preferably less than 0.10 wt. % (determined by Karl Fischer analysis). Moisture content is kept low in order to prevent hydrolysis of the aliphatic polyester and to give clarity to extruded film. The moisture level should be similarly controlled for solvent cast films that are dried at elevated temperatures, e.g. greater than 50° C.-60° C.

When used, the antimicrobial component content (as it is ready to use) is typically at least 1 wt. %, 2 wt. %, 5 wt. %, 10 wt. % and sometimes greater than 15 wt. %. In certain embodiments, for example in applications in which a low strength is desired, the antimicrobial component comprises greater than 20 wt. %, greater than 25 wt. %, or even greater than 30 wt. % of the composition.

Certain antimicrobial components are amphiphiles and may be surface active. For example, certain antimicrobial alkyl monoglycerides are surface active. For certain embodiments of the invention that include antimicrobial components, the antimicrobial component is considered distinct from a surfactant component.

The compositions may further comprise organic and inorganic fillers. For implantable applications biodegradable, resorbable, or bioerodible inorganic fillers may be particularly appealing. These materials may help to control the degradation rate of the polymer composition. For example, many calcium salts and phosphate salts may be suitable. Exemplary biocompatible resorbable fillers include calcium carbonate, calcium sulfate, calcium phosphate, calcium sodium phosphates, calcium potassium phosphates, tetracalcium phosphate, alpha-tricalcium phosphate, beta-tricalcium phosphate, calcium phosphate apatite, octacalcium phosphate, dicalcium phosphate, calcium carbonate, calcium oxide, calcium hydroxide, calcium sulfate dihydrate, calcium sulfate hemihydrate, calcium fluoride, calcium citrate, magnesium oxide, and magnesium hydroxide. A particularly suitable filler is tribasic calcium phosphate (hydroxy apatite).

Plasticizers may be used with the aliphatic polyester thermoplastic and include, for example, glycols such glycerin; propylene glycol, polyethoxylated phenols, mono or polysubstituted polyethylene glycols, higher alkyl substituted N-alkyl pyrrolidones, sulfonamides, triglycerides, citrate esters, esters of tartaric acid, benzoate esters, polyethylene glycols and ethylene oxide propylene oxide random and block copolymers having a molecular weight less than 10,000 daltons preferably less than about 5000 daltons, more preferably less than about 2500 daltons; and combinations thereof. As discussed above, the surfactant carrier can also function as a plasticizer, and may be distinct from a plasticizer added as an optional component.

Other additional components include antioxidant, colorant such as dyes and/or pigments, antistatic agents, fluorescent brightening agents, odor control agents, perfumes and fragrances, active ingredients to promote wound healing or other dermatological activity, combinations thereof and the like.

Applications and Methods of Manufacturing

Articles comprising the inventive composition may be made by processes known in the art for making products such as polymer sheets from polymer resins. For many applications, such articles can be placed in water at 23° C. without substantial loss of physical integrity (e.g. tensile strength) after being immersed 2 hours and dried. Typically, these articles contain little or no water. The water content in the article after extruding, injection molding or solvent casting is typically less than 10% by weight, preferably less than 5% by weight, more preferably less than 1% by weight and most preferably less than 0.2% by weight. Polymeric sheets may be formed by an extrusion process from the resin compositions described herein, resulting in hydrophilic polymer sheets useful in applications such as medical drapes and garments, personal care items and food wrapping.

Articles that may be made of the compositions may include medical drapes and gowns, including surgical drapes, procedural drapes, plastic specialty drapes, incise drapes, barrier drapes, barrier gowns, SMS gowns, and the like; wound dressings, wound absorbents, and wound contact layers; surgical sponges use to absorb blood and body fluids during surgery; surgical implants; as well as tubular extrusion products such as vascular catheters, urinary catheters, endotracheal tubes, shunts, wound drains and other medical devices.

Importantly the preferred hydrophilic additive surfactants of the compositions described herein allow for adhesive, thermal, and/or ultrasonic bonding of fabrics and films made thereof. Articles may be solvent, heat, or ultrasonically welded together as well as being welded to other compatible articles. The compositions may be used in conjunction with other materials to form constructions such as sheath/core materials, laminates, compound structures of two or more materials, or useful as coatings on various medical devices.

The compositions described herein are particularly suitable for use in surgical drapes and gowns due to their unique wetting properties. For example, the polylactic acid/surfactant compositions have durable hydrophilicity as described herein. Non-woven web and sheets comprising the inventive compositions have good tensile strength; can be heat sealed to form strong bonds allowing specialty drape fabrication; can be made from renewable resources which can be important in disposable products; and can have high surface energy to allow wettability and fluid absorbency in the case of non-wovens (as measured for nonwovens using the Apparent Surface Energy test and absorbing water); and for films the contact angles often are less than 50 degrees, preferably less than 30 degrees, and most preferably less than 20 degrees when the contact angles are measured using distilled water on a flat film using the half angle technique described in U.S. Pat. No. 5,268,733 and a Tantec Contact Angle Meter, Model CAM-micro, Schamberg, Ill. In order to determine the contact angle of materials other than films, a film of the exact same composition should be made by solvent casting.

It is believed that such non-woven, film and tube materials can be sterilized by gamma radiation or electron beam without significant loss of physical strength. A measure of physical strength can be tensile strength for a 1 mil thick film that does not decrease by more than 20%, and preferably by not more than 10%, after exposure to 2.5 Mrad gamma radiation from a cobalt gamma radiation source and aged at 23-25° C. for 7 days.

The hydrophilic characteristic of the inventive composition may improve articles such as wound and surgical dressings by improving absorbency. If the composition is used in a wound dressing backing film, the film may be partially (e.g. zone or pattern) coated or completely coated with various adhesives, including but not limited to pressure sensitive adhesives (PSAs), such as acrylic and block copolymer adhesives, hydrogel adhesives, hydrocolloid adhesives, and foamed adhesives.

PSAs can have a relatively high moisture vapor transmission rate to allow for moisture evaporation. Suitable pressure sensitive adhesives include those based on acrylates, polyurethanes, KRATON and other block copolymers, silicones, rubber based adhesives as well as combinations of these adhesives. The preferred PSAs are medical adhesives that are applied to skin such as the acrylate copolymers described in U.S. Pat. No. RE 24,906, the disclosure of which is hereby incorporated by reference, particularly a 97:3 iso-octyl acrylate:acrylamide copolymer. Also preferred is an 70:15:15 isooctyl acrylate-ethyleneoxide acrylate:acrylic acid terpolymer, as described in U.S. Pat. No. 4,737,410 (Example 31), the disclosure of which is hereby incorporated by reference. Other useful adhesives are described in U.S. Pat. Nos. 3,389,827; 4,112,213; 4,310,509; and 4,323,557; the disclosures of which are hereby incorporated by reference. Inclusion of medicaments or antimicrobial agents in the adhesive is also contemplated, as described in U.S. Pat. Nos. 4,310,509 and 4,323,557.

Other medical devices that may be made, in whole or in part, of the inventive composition include: sutures, suture fasteners, surgical mesh, slings, orthopedic pins (including bone filling augmentation material), adhesion barriers, stents, guided tissue repair/regeneration devices, articular cartilage repair devices, nerve guides, tendon repair devices, atrial septal defect repair devices, pericardial patches, bulking and filling agents, vein valves, bone marrow scaffolds, meniscus regeneration devices, ligament and tendon grafts, ocular cell implants, spinal fusion cages, skin substitutes, dural substitutes, bone graft substitutes, bone dowels, and hemostats.

The compositions of the present invention may also be useful in consumer hygiene products, such as adult incontinence, infant diapers, feminine hygiene products, and others as described in Applicants' co-pending application, U.S. Patent Application Publication No. 2008-0200890A1, and incorporated by reference herein in its entirety.

In one process for making the inventive composition, the aliphatic polyester in a melt form is mixed in a sufficient amount relative to the surfactant to yield a polymer composition having hydrophilic characteristics as described herein.

A variety of equipment and techniques are known in the art for melt processing polymeric compositions. Such equipment and techniques are disclosed, for example, in U.S. Pat. No. 3,565,985 (Schrenk et al.); U.S. Pat. No. 5,427,842 (Bland et. al.); U.S. Pat. No. 5,589,122 and U.S. Pat. No. 5,599,602 (Leonard); and U.S. Pat. No. 5,660,922 (Henidge et al.). Examples of melt processing equipment include, but are not limited to, extruders (single and twin screw), Banbury mixers, and Brabender extruders for melt processing the inventive composition.

The ingredients of the composition may be mixed in and conveyed through an extruder to yield a polymer composition, preferably without polymer degradation or side reactions in the melt. Potential degradation reactions include transesterification, hydrolysis, chain scission and radical chain decomposition, and process conditions should minimize such reactions. The processing temperature is sufficient to mix the aliphatic polyester and surfactant, and allow extruding the composition as a film. Films made with the compositions described herein have properties that are desirable in applications such as food wrap, e.g., transparent (not hazy) and being free of oily residue on the surface (which might indicate phase separation of components from the polymer matrix).

The compositions may be solvent cast into a film. The ingredients of the composition are typically dissolved or at least partially solvated, and thoroughly mixed in a suitable solvent which is then cast on a surface and allowed to evaporate, leaving solids comprising the hydrophilic durable resin composition.

The invention will be further clarified by the following examples which are exemplary and not intended to limit the scope of the invention.

Test Methods

Apparent Surface Energy

The method for measuring the surface energy is AATCC Test Method 118-1983, with the modifications described below. Surface energies measured according to this modified test method are hereinafter referred to as "apparent" surface energies. AATCC test method 118-1983 determines the surface energy of a fabric by evaluating the fabric's resistance to wetting by a series of selected hydrocarbon compositions. The hydrocarbons set forth in AATCC 118-1983, however, only provide for measurements of surface energy from about 19.8 to 27.3 dynes per centimeter at 25° C. This range is extended by employing various mixtures of methanol and water in the fabric resistance test. The compositions and their representative surface tensions are as follows:

| Liquid No. | Volume % Methanol/Water | Surface Tension (Dynes/cm at 20 C. |
|---|---|---|
| 7 | 65/45 | 30 |
| 8 | 53/47 | 35 |
| 9 | 40/60 | 40 |
| 10 | 25/75 | 45 |
| 11 | 21/79 | 50 |
| 12 | 15/85 | 55 |
| 13 | 8.5/91.5 | 60 |

The test procedure is as follows. A specimen of the covering material is placed flat on a smooth, horizontal surface. Using the method of AATCC 118-1983 except that beginning with the lowest number test liquid, 5 drops of the liquid are placed on the surface of the fabric on the side which will face the resin impregnated sheet in various locations. If three of the five drops wick into the fabric within 60 seconds, the liquid of the next higher surface energy is used. When at least 3 drops remain on the fabric surface the apparent surface tension is recorded as the range of the last two liquids.

EXAMPLES

Glossary of Terms

PLA 6202D Polylactic acid (Natureworks, Minnetonka, Minn.)
PLA 4032 Polylactic acid (Natureworks, Minnetonka, Minn.)
PLA 4060D Polylactic acid (Natureworks, Minnetonka, Minn.)
Brij 700 Steareth-100 (Sigma Aldrich, Milwaukee, Wis.)
Pationic 138C Sodium lauroyl lactylate (RITA Corporation, Crystal Lake, Ill.)

Carbowax 400 polyethylene glycol (PEG) 400 (Dow Chemical, Midland, Mich.)
PEG/DOSS 50% docusate sodium USP in PEG 400, (Cytec Industries, West Patterson, N.J.)
Hostapon STCI-85 Sodium cocoyl isethionate, 85%, (Clariant, Wayne N.J.)
Hostapur SAS-93G Sodium C14-C17 alkyl sec. sulfonate, (Clariant, Wayne N.J.)
Montanov 202 Arachidyl Alcohol (and) Behenyl Alcohol (and) Arachidyl Glucoside (Seppic, Fairfield, N.J.)
Citroflex A4 acetyl tributyl citrate (Morflex Inc., Greensboro, N.C.)
Crodaphos SG PPG-5 ceteth 10 phosphate (Croda, Inc., Parsipanny, N.J.)

Examples C1-C3, 1, and 2

The compositions listed in Table 1 were extruded on an experimental spunbond making line. The spunbond nonwovens were generally made using the equipment and processing techniques for spunbond nonwovens described in U.S. Pat. No. 6,916,752.

Non-woven spunbond PLA samples were made with different concentrations of surfactants. A non-woven spunbond PLA sample without any surfactant was also made. This was done for the purpose of evaluating and comparing the different samples' wettability, aging stability, and general mechanical properties.

The initial step was to pre-compound the wetting agents into higher concentration masterbatches. This was done using a 25 mm Berstorff UTX twin screw extruder, fitted with a standard pelletizing die. The strands were run through a 12 foot water bath and into a pelletizing puller.

Four masterbatches were made:
1) 95% PLA 6202D and 5% PEG 400
2) 95% PLA 6202D and 5% PEG/DOSS
3) 90% PLA 6202D and 10% Brij 700
4) 90% PLA 6202D and 10% Pationic 138C The PLA was fed using a K-tron Feeder. The other additives were all fed using a grid melter and were fed into Zone 4. Feed rates were as follows

| Batch | PLA 6202D Feed Rate (lbs/hr) | PEG400 Feed Rate (lbs/hr) | PEGDOSS Feed Rate (lbs/hr) | Brij 700 Feed Rate (lbs/hr) | Pationic 138C Feed Rate (lbs/hr) |
|---|---|---|---|---|---|
| 1 | 95 | 5 | | | |
| 2 | 95 | | 5 | | |
| 3 | 58.5 | | | 6.5 | |
| 4 | 61.2 | | | | 6.8 |

The zone temperatures were as follows:

After the strands passed through the water bath and the pelletizer, they were collected in 5 gallon pail liners, with holes in the bottom to allow any excess water to run off. The liners were placed in 5 gallon pails and were raised from the bottom about 4 inches. Once the samples had been "drip dried", the batches were distributed into multiple pans and allowed to crystallize in a batch oven at 65° C. for 12 to 24 hours.

The masterbatches and the virgin PLA were dried for a minimum of 6 hours in a recirculated drier at 60° C. A web was made with 60 g/sq/m. Melt temperatures were about 190-210° C. When running Masterbatch 4 with Pationic 138C, a dramatic viscosity reduction occurred, so the temperature had to be dropped 160° C. The webs were passed through a through air bonder on a screen support at a temperature of 90-100° C. in order lightly bond the web.

Spunbond nonwoven examples were prepared using the masterbatches described above blended with neat 6202D PLA. All the materials were dried prior to use. The spunbond nonwovens were obtained using a Davis-Standard BLUE RIBBON (DS-20®) extruder (Davis Standard Corporation, Pawcatuck, Conn.) using a 2.0 inch/50 mm single screw extruder to feed into through a pump to an extrusion head including multiple die orifices.

The die head had a total of 512 orifice holes with an aliphatic polyester polymer melt throughput of 0.50 g/hole/min (33.83 Ib/hr). The die had a transverse length of 7.875 inches (200 mm) The hole diameter was 0.040 inch (0.889 mm) and L/D ratio of 6. The melt extrusion temperature at the die of the neat PLA was set at 215° C., while the melt extrusion temperature of PLA with the surfactant additives was dependent on the type and amount of additives. The temperature was adjusted in order to make similar webs to the control (pure aliphatic polyester, PLA). A representative description of the web forming and bonding process is exemplified by U.S. Patent Application Publication No. US 2008/0038976 A1, and incorporated herein as reference in its entirety.

| Batch | Screw Speed (RPM) | Extrud. Amp | Extrud. KW | Zone 1 | Zone 2 | Zone 3 | Zone 4 | Zone 5 | Zone 6 | Zone 7 | Zone 8 | Zone 9 | Zone 10 | Die ° F. | Melt Temp- ° F. |
|---|---|---|---|---|---|---|---|---|---|---|---|---|---|---|---|
| 1 | 550 | 31.9 | 7 | 101.2 | 380 | 380 | 380 | 380 | 380 | 380 | 380 | 380 | 380 | 380 | 413 |
| 2 | 550 | 25.3 | 5.5 | 100.5 | 380 | 380 | 380 | 380 | 380 | 380 | 380 | 380 | 380 | 380 | 398.73 |
| 3 | 400 | 23.1 | 3.7 | 98.5 | 380 | 380 | 380 | 380 | 380 | 380 | 380 | 380 | 380 | 380 | 403.15 |
| 4 | 400 | 18.2 | 2.9 | 98.5 | 380 | 380 | 380 | 380 | 380 | 380 | 380 | 380 | 380 | 380 | 387.43 |

TABLE 1

| | Sample Composition | Aged at 5 C. Time (Days): | | | | | Aged at 45 C. | | | | |
|---|---|---|---|---|---|---|---|---|---|---|---|
| | | 0 Wet-Out Surface Tension (dynes/cm) | 7 Wet-Out Surface Tension (dynes/cm) | 14 Wet-Out Surface Tension (dynes/cm) | 28 Wet-Out Surface Tension (dynes/cm) | 42 Wet-Out Surface Tension (dynes/cm) | 0 Wet-Out Surface Tension (dynes/cm) | 7 Wet-Out Surface Tension (dynes/cm) | 14 Wet-Out Surface Tension (dynes/cm) | 28 Wet-Out Surface Tension (dynes/cm) | 42 Wet-Out Surface Tension (dynes/cm) |
| C1 | 95% PLA 6202D; 5% PEG-400 | 36 | 36 | 36 | 36 | 36 | 36 | N/A | N/A | N/A | N/A |
| C2 | 100% PLA 6202D | 36 | 36 | 36 | 36 | 36 | 36 | 36 | 36 | 36 | 36 |
| C3 | 95% PLA 6202D; 5% Brij 700 | 36 | 36 | 36 | 36 | 36 | 36 | 42 | 45 | 45 | 45 |
| 1 | 95% PLA 6202D; 5% DOSS/PEG | 72 | 72 | 72 | 72 | 72 | 72 | 72 | 72 | 72 | 72 |
| 2 | 95% PLA 6202D; 5% Pationic 138C | 72 | 72 | 72 | 72 | 72 | 72 | 72 | 72 | 72 | 72 |

The results indicate that virgin PLA (Comparative Example 2) is hydrophobic with an apparent surface energy of 36 dyne/cm throughout the aging at room temperature (23-25° C.) and ambient humidity. Addition of PEG 400 (MP<23° C.) or the surfactant Brij 700 (MP=51-54° C.) did not improve the hydrophilicity (Comparative Examples 1 and 3 respectively). Addition of the anionic surfactants docusate sodium (DOSS, MP=153-157° C.) and lauroyl lactylate (Pationic 138C, MP=50-55° C.) (Examples 1 and 2) resulted in a dramatic improvement in the hydrophilicity which was stable over time. The DOSS used was dissolved in a PEG 400 carrier (50% PEG400/50% DOSS solution, MP<23° C.) and formed a transparent solution which simplified processing and may have contributed to the superior hydrophilicity.

Examples C4-C5 and 3-5

Samples were prepared with PLA 4032 using a Brabender Hot Melt Mixer Model No. DR-2051. The Brabender was set to 200° C. and allowed to come to temperature. The paddle speed was set to 0.70. PLA 4032 was preweighed on a balance and added to the Brabender. Total mass of finished mixture was 60 g. PLA 4032 was mixed in the Brabender until a uniform, molten mixture was made while the specified mass of additives gradually added. Mixing times were typically 10-20 min. The Braebender chamber was purged using Unipurge purge resin (Dow Chemical, Midland, Mich.), after every run.

The molten mixtures were pulled from the Brabender and pressed into uniform sheets using a hydraulic press. Samples were pressed at 195° C. and with 20,000 lbs of pressure for 60 seconds between two liners. The liner was a silicone coated kraft paper release liner. Films were 50-125 micron thick.

Formulations of PLA 4032 with various surfactants are shown below in Table 2 along with the contact angle measurements.

TABLE 2

| Example | Surfactant | % Surf | Initial Contact Angle Measurements | | | | After 24 hrs at 72 C. | | | | Avg. Change |
|---|---|---|---|---|---|---|---|---|---|---|---|
| | | | 1 | 2 | 3 | Avg. Angle | 1 | 2 | 3 | Avg. Angle | |
| C4 | None | 0 | 60 | 68 | 66 | 64.66667 | 84 | 70 | 78 | 77.33333 | 12.66667 |
| C5 | Montanov 202 | 5 | 82 | 79 | 86 | 82.33333 | 58 | 66 | 46 | 56.66667 | −25.66667 |
| 3 | Pationic 138C | 5 | 10 | 10 | 10 | 10 | 10 | 10 | 10 | 10 | 0 |
| 4 | Hostapon STCI 85G | 5 | 58 | 52 | 54 | 54.66667 | 34 | 46 | 30 | 36.66667 | −18 |
| 5 | Hostapur SAS-93G | 5 | 10 | 10 | 10 | 10 | 30 | 28 | 30 | 29.33333 | 19.33333 |

The virgin PLA was relatively hydrophobic. Addition of Montanov 202 did not result in a hydrophilic film. Even after heating the contact angle was still greater than 50 degrees. The Pationic (alkyl carboxylate) resulted in a very hydrophilic film and heating to 72° C. did not alter the result. The two sulfonate surfactants behaved differently. The isethionate surfactant produced a film which was initially relatively hydrophobic but after heating the contact angle decreased to 37 degrees. The C14-C17 alkyl sulfonate (Hostapur SAS) produced a hydrophilic film, however, aging for 24 hrs at 72° C. increased the contact angle to 29 degrees. The inventive compositions resisted fogging when breathed on.

Examples 6-8

The following samples were made and tested according to the procedure described in Examples C4-C5 and Examples 3-5 above.

TABLE 3

| | Example Number | | |
|---|---|---|---|
| Component | 6 | 7 | 8 |
| Natureworks PLA 4060D | 75 | 70 | 75 |
| Citroflex A4 | 20 | 20 | 20 |

TABLE 3-continued

|  | Example Number | | |
|---|---|---|---|
| Component | 6 | 7 | 8 |
| Crodafos SG | 5 | 10 | 2.5 |
| triethanolamine | 0 | 0 | 2.5 |
| Total | 100 | 100 | 100 |
| Contact angle | 30 | 23 | 22 |
| Contact angle | 28 | 18 | 22 |
| Contact angle | 22 | 26 | 20 |
| Average Contact angle | 26.7 | 22.3 | 21.3 |

These results show that the alkoxylated phosphate surfactant, Crodafos SG, improved the hydrophilicity significantly. In comparison, the contact angle of PLA with Citroflex plasticizer and no surfactant is still very hydrophobic, having a contact angle in excess of 60 degrees (data not shown). The addition of Crodaphos SG in the acid form (Example 6) reduced the contact angle to less than 27. Addition of more Crodaphos SG (Example 7) reduced the contact angle further and neutralization with triethanolamine to make the phosphate salt reduced the contact angle further yet (Example 8).

While certain representative embodiments and details have been discussed above for purposes of illustrating the invention, various modifications may be made in this invention without departing from its true scope, which is indicated by the following claims.

The invention claimed is:

1. A nonwoven web of fibers, wherein the fibers comprise a blend comprising:
at least one thermoplastic aliphatic polyester;
an alkyl, alkenyl, aralkyl, or alkaryl anionic surfactant incorporated in the polyester; wherein the surfactant is selected from the group consisting of alkyl sulfate, alkenyl sulfate, alkaryl sulfate, aralkyl sulfate, alkylalkoxylated sulfate, alkyl sulfonate, alkenyl sulfonate, alkaryl sulfonate, aralkyl sulfonate, alkylalkoxylated sulfonate, alkyl phosphonate, alkenyl phosphonate, alkaryl phosphonate, aralkyl phosphonate, alkyl phosphate, alkenyl phosphate, alkaryl phosphate, aralkyl phosphate, alkyl alkoxylated phosphate, di($C_8$-$C_{18}$) sulfosuccinate salts, $C_8$-$C_{22}$ alkyl sarcosinate salts, $C_8$-$C_{22}$ alkyl lactylate salts, and combinations thereof; wherein the surfactant is present in a concentration sufficient to make the nonwoven web durably hydrophilic and absorbent and instantaneously wettable; and
a surfactant carrier;
wherein the fibers are 20 micrometers or less in diameter;
wherein the surfactant is soluble in the carrier at greater than 10% by weight such that the surfactant and carrier form a visually transparent solution in a 1-cm path length glass vial when heated to 150° C.

2. The nonwoven web of claim 1 wherein the surfactant carrier is a liquid at 23° C.

3. The nonwoven web of claim 1 wherein the anionic surfactant has a melting point of less than 200° C.

4. The nonwoven web of claim 1 wherein the anionic surfactant is selected from the group consisting of di($C_8$-$C_{18}$) sulfosuccinate salts, $C_8$-$C_{22}$ alkyl sarcosinate salts, alkyl alkoxylated phosphates, $C_8$-$C_{22}$ alkyl lactylate salts, and combinations thereof.

5. The nonwoven web of claim 1 wherein the anionic surfactant is present in a total amount of at least 0.5 wt-% of the blend.

6. The nonwoven web of claim 5 wherein the anionic surfactant is present in an amount of at least 0.5% by weight and no greater than 8% by weight of the blend.

7. The nonwoven web of claim 1 wherein the web is instantaneously absorbent.

8. The nonwoven web of claim 1 wherein the thermoplastic aliphatic polyester is selected from the group consisting of one or more poly(lactic acid), poly(glycolic acid), poly(lactic-co-glycolic acid), polybutylene succinate, polyhydroxybutyrate, polyhydroxyvalerate, blends, and copolymers thereof.

9. The nonwoven web of claim 1 wherein the surfactant carrier is selected from the group consisting of polyalkylene glycols, polyhydric alcohols, glycerin triglcyerides, citric acid esters, aliphatic diesters, and combinations thereof.

10. The nonwoven web of claim 1 wherein the nonwoven web is selected from the group consisting of a spunbond web, a blown microfiber web, and a hydroentangled web.

11. The nonwoven web of claim 1 wherein the surfactant is soluble in the carrier at greater than 10% by weight such that the surfactant and carrier form a visually transparent solution in a 1-cm path length glass vial at less than 100° C.

12. An article comprising a non-woven web of fibers, wherein the fibers comprise a blend comprising:
at least one thermoplastic aliphatic polyester present in a concentration of at least 75%, wherein the thermoplastic aliphatic polyester is selected from the group consisting of one or more poly(lactic acid), poly(glycolic acid), poly(lactic-co-glycolic acid), polybutylene succinate, polyhydroxybutyrate, polyhydroxyvalerate, blends, and copolymers thereof; and
a phosphate surfactant incorporated into the polyester, wherein the phosphate is selected from the group consisting of alkyl, alkaryl, alkenyl or aralkyl phosphates, and alkyl alkoxylated phosphates; wherein the phosphate surfactant is present in a concentration sufficient to make the nonwoven web durably hydrophilic and absorbent and instantaneously wettable;
wherein the fibers are 20 micrometers or less in diameter;
wherein the nonwoven is a blown microfiber web.

13. The article of claim 12, wherein the phosphate has one of the following structures:

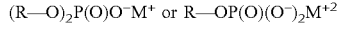

wherein:
R=alkyl or alkylene of C8-C30 which is branched or straight chain, or C12-C30 aralkyl, and may be optionally substituted with 0-100 alkylene oxide groups; and
M=an alkali metal salt or an amine salt.

14. The article of claim 12, wherein the phosphate is present in an amount no greater than 8% by weight of the composition, and wherein the anionic surfactant is present in an amount of at least 0.5% by weight of the composition.

15. The article of claim 12, wherein the fibers further comprise a surfactant carrier and wherein the surfactant carrier is present in an amount no greater than 8% by weight of the composition.

16. The article of claim 12, wherein the fibers further comprise an antimicrobial component.

17. The article of claim 12, wherein the article is a surgical drape or a surgical gown.

18. The article of claim 12, wherein the article is a wound contact material or a personal hygiene article.

19. The article of claim 12, further comprising a layer bonded to the non-woven web of fibers.

20. The article of claim 19, wherein the layer is thermally bonded to the non-woven web of fibers.

21. The article of claim 19, wherein the layer is adhesively bonded to the non-woven web of fibers.

22. The article of claim 19, wherein the layer comprises a polymeric film.

23. The article of claim 19, wherein the layer comprises a woven or non-woven web.

24. The nonwoven web of claim 1, wherein the aliphatic polyester comprises greater than 75 wt % of the fibers.

25. The article of claim 12, wherein the aliphatic polyester comprises greater than 75 wt % of the fibers.

\* \* \* \* \*

UNITED STATES PATENT AND TRADEMARK OFFICE
CERTIFICATE OF CORRECTION

PATENT NO. : 10,138,576 B2
APPLICATION NO. : 14/487134
DATED : November 27, 2018
INVENTOR(S) : Matthew Scholz et al.

Page 1 of 2

It is certified that error appears in the above-identified patent and that said Letters Patent is hereby corrected as shown below:

In the Specification

Column 1
Line 35, Delete "polybutylene" and insert -- poly(butylene --, therefor.
Line 46, Delete "spunbound" and insert -- spunbond --, therefor.

Column 5
Line 63, Delete "arakyl" and insert -- aralkyl --, therefor.
Line 64, Delete "arakyl" and insert -- aralkyl --, therefor.
Line 64, Delete "arakyl" and insert -- aralkyl --, therefor.
Line 65, Delete "arakyl" and insert -- aralkyl --, therefor.

Column 7
Line 11, Delete "(Shaumburg," and insert -- (Schaumburg, --, therefor.

Column 8
Line 16, Delete "caternary" and insert -- catenary --, therefor.
Line 61, Delete "caternary" and insert -- catenary --, therefor.

Column 10
Line 66, Delete "arakyl" and insert -- aralkyl --, therefor.

Column 11
Line 12, Delete "sarconsinate;" and insert -- sarcosinate; --, therefor.
Line 24, Delete "oligameric" and insert -- oligomeric --, therefor.
Line 35 (approximately), Delete "lacylate" and insert -- lactylate --, therefor.
Line 44, Delete "Cetheth-10" and insert -- Ceteth-10 --, therefor.
Line 45, Delete "(Crodaphos" and insert -- (Crodafos --, therefor.
Line 63 (approximately), Delete ")$_{m3}(O)_b$" and insert -- )$_{m3}$-(O)$_b$ --, therefor.

Signed and Sealed this
Fourteenth Day of April, 2020

Andrei Iancu
*Director of the United States Patent and Trademark Office*

Column 12
Line 33, Delete "LANTHANOL" and insert -- LATHANOL --, therefor.
Line 60, Delete "Parsipanny," and insert -- Parsippany, --, therefor.

Column 13
Line 66, Delete "propyelene" and insert -- propylene --, therefor.

Column 14
Line 1, Delete "dipropyeleneglycol" and insert -- dipropyleneglycol --, therefor.
Line 20, Delete "tetraetheylene" and insert -- tetraethylene --, therefor.
Line 30-31, Delete "pentaerithritol," and insert -- pentaerythritol, --, therefor.

Column 16
Line 50, Delete "Schamberg," and insert -- Schaumburg, --, therefor.

Column 19
Line 14 (approximately), Delete "Parsipanny," and insert -- Parsippany, --, therefor.

Column 21
Line 62, Delete "Braebender" and insert -- Brabender --, therefor.

In the Claims

Column 24
Line 14 (approximately), In Claim 9, delete "triglcyerides," and insert -- triglycerides, --, therefor.